(12) United States Patent
Razzaque et al.

(10) Patent No.: US 9,282,947 B2
(45) Date of Patent: Mar. 15, 2016

(54) IMAGER FOCUSING BASED ON INTRAOPERATIVE DATA

(75) Inventors: Sharif Razzaque, Chapel Hill, NC (US); Andrei State, Chapel Hill, NC (US); Kurtis Keller, Hillsborough, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 1189 days.

(21) Appl. No.: 12/949,449

(22) Filed: Nov. 18, 2010

(65) Prior Publication Data

US 2011/0130641 A1 Jun. 2, 2011

Related U.S. Application Data

(60) Provisional application No. 61/265,517, filed on Dec. 1, 2009, provisional application No. 61/265,521, filed on Dec. 1, 2009.

(51) Int. Cl.
*A61B 5/05* (2006.01)
*A61B 8/08* (2006.01)
*A61B 8/00* (2006.01)
(Continued)

(52) U.S. Cl.
CPC ............. *A61B 8/5238* (2013.01); *A61B 8/0833* (2013.01); *A61B 8/0841* (2013.01); *A61B 8/4245* (2013.01); *A61B 5/06* (2013.01); *A61B 8/4254* (2013.01); *G01S 7/52034* (2013.01);
(Continued)

(58) Field of Classification Search
CPC .... A61B 8/0833; A61B 8/0841; A61B 8/483; G01S 7/52034; G01S 15/8979; G01S 15/8988; G01S 15/8993
See application file for complete search history.

(56) References Cited

U.S. PATENT DOCUMENTS

RE30,397 E 9/1980 King
4,294,544 A 10/1981 Altschuler et al.
(Continued)

FOREIGN PATENT DOCUMENTS

CN 1636520 7/2005
CN 100381108 4/2008
(Continued)

OTHER PUBLICATIONS

U.S. Appl. No. 11/828,826, filed Jul. 26, 2007, Kurtis P. Keller et al.
(Continued)

*Primary Examiner* — Joel Lamprecht
(74) *Attorney, Agent, or Firm* — Knobbe, Martens, Olson & Bear, LLP

(57) ABSTRACT

Various embodiments herein provide for imager focusing based on intraoperative data. Ideally, an imaging plane of an ultrasound transducer would be truly planar. That is not the case, though. Instead, ultrasound transducers image a volume that is closer to a rectangular volume, but that has focal depths or areas in the imaged volume that are "thinner" and provide a better resolution. In general, embodiments herein may include determining the pose of an imager, such as an ultrasound transducer, and the pose of a location of interest. Based on those poses, a focal adjustment may be determined in order to, for example, better focus the imager on the object of interest. Then data is generated and the focus of the imager is adjusted. Additionally, imaging data and/or the object of interest may be displayed. In other embodiments, estimated projections of medical devices are displayed to allow for better intraoperative planning.

18 Claims, 12 Drawing Sheets

(51) Int. Cl.
   *G01S 7/52*       (2006.01)
   *G01S 15/89*     (2006.01)
   *A61B 5/06*       (2006.01)

(52) U.S. Cl.
   CPC ......... *G01S 15/8979* (2013.01); *G01S 15/8988* (2013.01); *G01S 15/8993* (2013.01)

(56) References Cited

U.S. PATENT DOCUMENTS

| | | |
|---|---|---|
| 4,862,873 A | 9/1989 | Yajima et al. |
| 4,884,219 A | 11/1989 | Waldren |
| 5,109,276 A | 4/1992 | Nudelman et al. |
| 5,193,120 A | 3/1993 | Gamache et al. |
| 5,249,581 A | 10/1993 | Horbal et al. |
| 5,261,404 A | 11/1993 | Mick et al. |
| 5,307,153 A | 4/1994 | Maruyama et al. |
| 5,323,002 A | 6/1994 | Sampsell et al. |
| 5,371,543 A | 12/1994 | Anderson |
| 5,383,454 A | 1/1995 | Bucholz |
| 5,446,798 A | 8/1995 | Morita et al. |
| 5,452,024 A | 9/1995 | Sampsell |
| 5,457,493 A | 10/1995 | Leddy et al. |
| 5,488,431 A | 1/1996 | Gove et al. |
| 5,489,952 A | 2/1996 | Gove et al. |
| 5,491,510 A | 2/1996 | Gove |
| 5,517,990 A | 5/1996 | Kalfas et al. |
| 5,526,051 A | 6/1996 | Gove et al. |
| 5,532,997 A | 7/1996 | Pauli |
| 5,541,723 A | 7/1996 | Tanaka |
| 5,570,135 A | 10/1996 | Gove et al. |
| 5,579,026 A | 11/1996 | Tabata |
| 5,588,948 A | 12/1996 | Takahashi et al. |
| 5,608,468 A | 3/1997 | Gove et al. |
| 5,611,353 A | 3/1997 | Dance et al. |
| 5,612,753 A | 3/1997 | Poradish et al. |
| 5,625,408 A | 4/1997 | Matsugu et al. |
| 5,629,794 A | 5/1997 | Magel et al. |
| 5,630,027 A | 5/1997 | Venkateswar et al. |
| 5,699,444 A | 12/1997 | Palm |
| 5,726,670 A | 3/1998 | Tabata et al. |
| 5,766,135 A | 6/1998 | Terwilliger |
| 5,784,098 A | 7/1998 | Shoji et al. |
| 5,807,395 A | 9/1998 | Mulier et al. |
| 5,820,554 A | 10/1998 | Davis et al. |
| 5,870,136 A | 2/1999 | Fuchs et al. |
| 5,891,034 A | 4/1999 | Bucholz |
| 6,019,724 A | 2/2000 | Gronningsaeter et al. |
| 6,048,312 A * | 4/2000 | Ishrak et al. ............. 600/443 |
| 6,064,749 A | 5/2000 | Hirota et al. |
| 6,095,982 A | 8/2000 | Richards-Kortum et al. |
| 6,108,130 A | 8/2000 | Raj |
| 6,167,296 A | 12/2000 | Shahidi |
| 6,216,029 B1 | 4/2001 | Paltieli |
| 6,246,898 B1 | 6/2001 | Vesely et al. |
| 6,261,234 B1 | 7/2001 | Lin |
| 6,341,016 B1 | 1/2002 | Malione |
| 6,348,058 B1 | 2/2002 | Melken et al. |
| 6,385,475 B1 | 5/2002 | Cinquin et al. |
| 6,442,417 B1 | 8/2002 | Shahidi et al. |
| 6,456,868 B2 | 9/2002 | Saito et al. |
| 6,470,207 B1 | 10/2002 | Simon et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,587,711 B1 | 7/2003 | Alfano et al. |
| 6,591,130 B2 | 7/2003 | Shahidi |
| 6,594,517 B1 | 7/2003 | Nevo |
| 6,597,818 B2 | 7/2003 | Kumar et al. |
| 6,689,067 B2 | 2/2004 | Sauer et al. |
| 6,725,082 B2 | 4/2004 | Sati et al. |
| 6,733,458 B1 | 5/2004 | Steins et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,873,867 B2 | 3/2005 | Vilsmeier |
| 6,881,214 B2 | 4/2005 | Cosman et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,947,783 B2 | 9/2005 | Immerz |
| 7,033,360 B2 | 4/2006 | Cinquin et al. |
| 7,072,707 B2 | 7/2006 | Galloway, Jr. et al. |
| 7,110,013 B2 | 9/2006 | Ebersole et al. |
| 7,209,776 B2 | 4/2007 | Leitner |
| 7,248,232 B1 | 7/2007 | Yamazaki et al. |
| 7,331,932 B2 | 2/2008 | Leitner |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,480,533 B2 | 1/2009 | Cosman et al. |
| 7,652,259 B2 * | 1/2010 | Kimchy et al. .......... 250/370.08 |
| 7,728,868 B2 | 6/2010 | Razzaque et al. |
| 7,797,032 B2 * | 9/2010 | Martinelli et al. ............. 600/424 |
| 8,167,805 B2 * | 5/2012 | Emery et al. ................... 600/439 |
| 2001/0007919 A1 | 7/2001 | Shahidi |
| 2001/0016804 A1 | 8/2001 | Cunningham et al. |
| 2001/0045979 A1 | 11/2001 | Matsumoto et al. |
| 2002/0010384 A1 | 1/2002 | Shahidi et al. |
| 2002/0049375 A1 | 4/2002 | Strommer et al. |
| 2002/0077540 A1 | 6/2002 | Kienzie, III |
| 2002/0077543 A1 | 6/2002 | Grzeszczuk et al. |
| 2002/0138008 A1 | 9/2002 | Tsujita et al. |
| 2002/0198451 A1 | 12/2002 | Carson |
| 2003/0040743 A1 | 2/2003 | Cosman et al. |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0095507 A1 | 5/2004 | Bishop et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243148 A1 | 12/2004 | Wasielewski |
| 2005/0085717 A1 | 4/2005 | Shahidi |
| 2005/0085718 A1 | 4/2005 | Shahidi |
| 2005/0090742 A1 | 4/2005 | Mine et al. |
| 2005/0111733 A1 | 5/2005 | Fors et al. |
| 2005/0159641 A1 | 7/2005 | Kanai |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0251148 A1 | 11/2005 | Friedrich |
| 2006/0004275 A1 | 1/2006 | Vija et al. |
| 2006/0036162 A1 | 2/2006 | Shahidi et al. |
| 2006/0052792 A1 | 3/2006 | Boettiger et al. |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0032906 A1 | 2/2007 | Sutherland et al. |
| 2007/0167699 A1 | 7/2007 | Lathuiliere et al. |
| 2007/0167701 A1 | 7/2007 | Sherman |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0270718 A1 | 11/2007 | Rochetin et al. |
| 2007/0276234 A1 | 11/2007 | Shahidi |
| 2008/0004516 A1 | 1/2008 | DiSilvestro et al. |
| 2008/0030578 A1 | 2/2008 | Razzaque et al. |

(56) References Cited

U.S. PATENT DOCUMENTS

| | | | |
|---|---|---|---|
| 2008/0051910 | A1 | 2/2008 | Kammerzell et al. |
| 2008/0091106 | A1 | 4/2008 | Kim et al. |
| 2008/0161824 | A1 | 7/2008 | McMillen |
| 2008/0200794 | A1 | 8/2008 | Teichman et al. |
| 2008/0208081 | A1 | 8/2008 | Murphy et al. |
| 2008/0214932 | A1 | 9/2008 | Mollard et al. |
| 2008/0287805 | A1 | 11/2008 | Li |
| 2009/0226069 | A1 | 9/2009 | Razzaque et al. |
| 2009/0312629 | A1 | 12/2009 | Razzaque et al. |
| 2010/0198045 | A1 | 8/2010 | Razzaque et al. |

FOREIGN PATENT DOCUMENTS

| | | |
|---|---|---|
| EP | 1955284 | 8/2008 |
| JP | 2005-058584 | 3/2005 |
| JP | 2005-323669 | 11/2005 |
| JP | 2009-517177 | 4/2009 |
| WO | PCT/US2003/17987 | 12/2003 |
| WO | WO 2007-067323 A2 | 6/2007 |
| WO | PCT/US2009/032028 | 1/2009 |
| WO | WO 2009-094646 | 7/2009 |
| WO | WO 2010-096419 | 8/2010 |

OTHER PUBLICATIONS

"3D Laparoscope Technology," http://www.inneroptic.com/tech_3DL.htm, copyright 2007 InnerOptic Technology, Inc. printed Sep. 19, 2007, 2 pages.

"Cancer Facts & Figures 2004," www.cancer.org/downloads/STT/CAFF_finalPWSecured.pdf, copyright 2004 American Cancer Society, Inc., printed Sep. 19, 2007, 60 pages.

"David Laserscanner (-Latest News (-Institute for Robotics and Process Control (-Te . . . ," http://www/rob.cs.tu-bs.de/en/news/david, printed Sep. 19, 2007, 1 page.

"Laser scanned 3d model Final" video, still image of video attached, http://www.youtube.com/watch?v+DaLgIgmoUf8, copyright 2007 YouTube, LLC, printed Sep. 19, 2007, 2 pages.

"Olympus Endoscopic Ultrasound System," www.olympusamerica.com/msg_section/download_brochures/135_b_gfum130.pdf, printed Sep. 20, 2007, 20 pages.

"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.

"Robbins, Mike—Computer Vision Research—Stereo Depth Perception," http://www.compumike.com/vision/stereodepth.php, copyright 2007 Michael F. Robbins, printed Sep. 19, 2007, 3 pages.

"RUE: Registered Ultrasound-Endoscope," copyright 2007 InnerOptic Technology, Inc., 2 pages.

Advertisement, "Inspeck 3DC 3D Capturor," Inspeck 3DC 3D Capturor (www.inspeck.com), 1998.

Advertisement, "Virtual 3D High Speed Non-Contact Surface Perception," Virtual 3-D Technologies Corporation (www.virtual3dtech.com)., Dec. 21, 1998.

Advertisements, "Virtuoso," Visual Interface, Inc. (www.visint.com), Dec. 21, 1998.

Akka, "Automatic Software Control of Display Parameters for Stereoscopic Graphics Images," SPIE vol. 1669: Stereoscopic Displays and Applications III, pp. 31-38 (1992).

Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.

Andrei State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.

Andrei State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.

Andrei State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 20007, 10 pages.

Andrei State et al., "Technologies for Augmented Reality Systems: Realizing Ultrasound-Guided Needle Biopsies," Computer Graphics, Proceedings of SIGGRAPH 1996, pp. 429-438, available from www.cs.princeton.edu/courses/archive/fall01/cs597d/papers/state96.pdf, printed Sep. 20, 2007.

Aylward et al., Analysis of the Parameter Space of a Metric for Registering 3D Vascular Images, in W. Niessen and M. Viergever (Eds.): MICCAI 2001, LNCS 2208, pp. 932-939, 2001.

Aylward et al., Registration and Analysis of Vascular Images, International Journal of Computer Vision 55(2/3), 123-138, 2003.

Azuma, "A Survey of Augmented Reality," Presence: Teleoperators and Virtual Environments 6, 4:1-48 (Aug. 1997).

Bajura, Michael et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.

Benavides et al., "Multispectral digital colposcopy for in vivo detection of cervical cancer," Optics Express; May 19, 2003; 11(1 0) Optical Society of America; USA.

Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.

Billinghurst, M. et al., Research Directions in Handheld AR; Int. J. of Virtual Reality 5(2),51-58 (2006).

Bishop, Azum R., G.; Improving Static and Dynamic Registration in an Optical See-Through HMO; Proceedings of SIGGRAPH '94, Computer Graphics, Annual Conference Series, 1994, 197-204 (1994).

Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.

Bouguet, Jean-Yves, "Camera Calibration Toolbox for Matlab," www.vision.caltech.edu/bouguety/calib_doc, printed Sep. 20, 2007, 5 pages.

Buxton et al.; "Colposcopically directed punch biopsy: a potentially misleading investigation," British Journal of Obstetrics and Gynecology; Dec. 1991; 98:1273-1276.

Cancer Prevention & Early Detection Facts & Figures 2004; National Center for Tobacco-Free Kids; 2004; American Cancer Society; USA.

Cantor et al., "Cost-Effectiveness Analysis of Diagnosis and Management of Cervical Squamous Intraepithelial Lesions," Diagnostic Strategies for SILs; Feb. 1998; 91(2):270-277.

Catalano et al., "Multiphase helical CT findings after percutaneous ablation procedures for hepatocellular carcinoma." Abdom. Imaging, 25(6),2000, pp. 607-614.

Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.

Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.

Deering, Michael "High Resolution Virtual Reality." Proceedings of SIGGRAPH '92, Computer Graphics, 26(2), 1992, pp. 195-202.

Depiero et al., "3-D Computer Vision Using Structured Light: Design, Calibration and Implementation Issues," The University of Tennessee, pp. 1-46, (1996).

(56) References Cited

OTHER PUBLICATIONS

Dodd, G.D. et al. "Minimally invasive treatment of malignant hepatic tumors: at the threshold of a major breakthrough." Radiographies 20(1),2000, pp. 9-27.

Drascic et al., "Perceptual Issues in Augmented Reality," SPIE vol. 2653: Stereoscopic Displays and Virtual Reality Systems III, pp. 123-134 (Feb. 1996).

Fahey et al., "Meta-analysis of Pap Test Accuracy; American Journal of Epidemiology," 1995 141(7):680-689; The John Hopkins University School of Hygiene and Public Health; USA.

Foxlin et al., An Inertial Head-Orientation Tracker with Automatic Drift Compensation for Use with HMD's, in Virtual Reality Software & Technology, Proceedings of the VRST Conference, pp. 159-173, Singapore, Aug. 23-26, 1994.

Fronheiser et al., Real-Time 3D Color Doppler for Guidance of Vibrating Interventional Devices, IEEE Ultrasonics Symposium, pp. 149-152 (2004).

Fuchs, Henry et al., "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis_LaparoSurg9.

Garrett, William F. et al., "Real-Time Incremental Visualization of Dynamic Ultrasound Volumes Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Georgakoudi et al., "Trimodal spectroscopy for the detection and characterization of cervical precancers in vivo," American Journal of Obstetrics and Gynecology; Mar. 2002; 186(3):374-382; USA.

Herline et al., Surface Registration for Use in Interactive, Image-Guided Liver Surgery, Computer Aided Surgery 5:11-17 (2000).

Holloway, R.; Registration Error Analysis for Augmented Reality; Presence: Teleoperators and Virtual Environments 6(4), 413-432 (1997).

Hornung et al., "Quantitative near-infrared spectroscopy of cervical dysplasia in vivo," Human Reproduction; 1999; 14(11):2908-2916; European Society of Human Reproduction and Embryology.

Howard et al., An Electronic Device for Needle Placement during Sonographically Guided Percutaneous Intervention, Radiology 2001; 218:905-911.

InnerAim Brochure; 3D Visualization Software for Simpler, Safer, more Precise Aiming, Published no earlier than Apr. 1, 2010.

International Search Report and Written Opinion received in corresponding PCT Application No. PCT/US2010/024378, mailed Oct. 13, 2010, 9 pages.

InVision System Brochure; A "GPS" for Real-Time 3D Needle Visualization & Guidance, Published no earlier than Mar. 1, 2008.

InVision User Manual; Professional Instructions for Use, Published no earlier than Dec. 1, 2008.

Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.

Kanbara et al., "A Stereoscopic Video See-through Augmented Reality System Based on Real-time Vision-Based Registration," Nara Institute of Science and Technology, pp. 1-8 (2000).

Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.

Lee et al., "Modeling Real Objects Using Video See-Through Augmented Reality," Presence, 11(2):144-157 (Apr. 2002).

Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.

Levy et al., An Internet-Connected, Patient Specific, Deformable Brain Atlas Integrated into a Surgical Navigation System, Journal of Digital Imaging, vol. 10, No. 3. Suppl. 1 (Aug. 1997): pp. 231-237.

Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.

Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).

Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 9 pages.

Milgram et al., "Adaptation Effects in Stereo due to Online Changes in Camera Configuration," SPIE vol. 1669-13, Stereoscopic Displays and Applications III, pp. 1-12 (1992).

Mitchell et al., "Colposcopy for the Diagnosis of Squamous Intraepithelial lesions: A metaanalysis," Obstetrics and Gynecology; Apr. 1998; 91(4):626-631.

Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.

Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.

Ohbuchi et al., "An Incremental Volume Rendering Algorithm for Interactive 3D Ultrasound Imaging", UNC-CH Computer Science Technical Report TR91-003, (1991).

Ohbuchi et al., "Incremental Volume Reconstruction and Rendering for 3D Ultrasound Imaging," Visualization in Biomedical Computing, SPIE Proceedings, pp. 312-323, (Oct. 13, 1992).

Ohbuchi, "Incremental Acquisition and Visualization of 3D Ultrasound Images," Ph.D. Dissertation, UNC-CH Computer Science Technical Report TR95-023, (1993).

PCT, The International Search Report of the International Searching Authority, mailed Mar. 3, 2011, for case PCT/US2010/043760.

PCT, The International Search Report of the International Searching Authority, mailed Sep. 9, 2009, for case PCT/US2009/032028.

PCT, The Written Opinion of the International Searching Authority, mailed Mar. 3, 2011, for case PCT/US2010/043760.

PCT. The Written Opinion of the International Searching Authority, mailed Sep. 9, 2009, for case PCT/US2009/032028.

Progue, Brian W. et al., "Analysis of acetic acid-induced whitening of high-grade squamous intraepitheliallesions," Journal of Biomedical Optics; Oct. 2001; 6(4):397-403.

Raij, A.B., et al., Comparing Interpersonal Interactions with a Virtual Human to Those with a Real Human; IEEE Transactions on Visualization and Computer Graphics 13(3), 443-457 (2007).

Raz et al, Real-Time Magnetic Resonance Imaging—Guided Focal Laser Therapy in Patients with Low-Risk Prostate Cancer, European Urology 58, pp. 173-177. Mar. 12, 2010.

Robinett et al., "A Computational Model for the Stereoscopic Optics of a Head-Mounted Display," SPIE vol. 1457, Stereoscopic Displays and Applications II, pp. 140-160 (1991).

Rolland et al., Towards Quantifying Depth and Size Perception in Virtual Environments, Presence: Teleoperators and Virtual Environments, Winter 1995, vol. 4, Issue 1, pp. 24-49.

Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248.

Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/.

Splechtna, Fuhrmann A. et al., Comprehensive calibration and registration procedures for augmented reality; Proc. Eurographics Workshop on Virtual Environments 2001,219-228 (2001).

(56) References Cited

OTHER PUBLICATIONS

State, Andrei et al., "Stereo Imagery from the UNC Augmented Reality System for Breast Biopsy Guidance" Proc. Medicine Meets Virtual Reality (MMVR) 2003, Newport Beach, CA, Jan. 22-25, 2003.

State, Andrei "Exact Eye Contact with Virtual Humans." Proc. IEEE International Workshop on Human Computer Interaction 2007 (Rio de Janeiro, Brazil, Oct. 20, 2007), pp. 138-145.

State, Andrei et al., "Interactive Volume Visualization on a Heterogenous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007, 7 pages.

Takagi et al., "Development of a Stereo Video See-through HMD for AR Systems," IEEE, pp. 68-77 (2000).

Ultraguide 1000 System, Ultraguide, www.ultraguideinc.com, 1998.

van Staveren et al., "Light Scattering in Intralipid-10% in the wavelength range of 400-1100 nm," Applied Optics; Nov. 1991; 30(31):4507-4514.

Viola et al., "Alignment by Maximization of Mutual Information," International Journal of Computer Vision, vol. 24, No. 2, pp. 1-29 (1997).

Viola, Paul A., Alignment by Maximization of Mutual Information, Ph.D. Dissertation, MIT—Artificial Intelligence Laboratory Technical Report No. 1548 (Jun. 1995).

Ware et al., "Dynamic Adjustment of Stereo Display Parameters," IEEE Transactions on Systems, Many and Cybernetics, 28(1):1-19 (1998).

Watson et al., "Using Texture Maps to Correct for Optical Distortion in Head-Mounted Displays," Proceedings of the Virtual Reality Annual Symposium '95, IEEE, pp. 1-7 (1995).

Welch, Hybrid Self-Tracker: An Inertial/Optical Hybrid Three-Dimensional Tracking System, University of North Carolina Chapel Hill Department of Computer Science, TR 95-048.(1995).

Yinghui Che, et al.,Real-Time Deformation Using Modal Analysis on Graphics Hardware, Graphite 2006, Kuala Lumpur, Malaysia, Nov. 29-Dec. 2, 2006.

Zitnick et al., "Multi-Base Stereo Using Surface Extraction," Visual Interface Inc., (Nov. 24, 1996).

\* cited by examiner

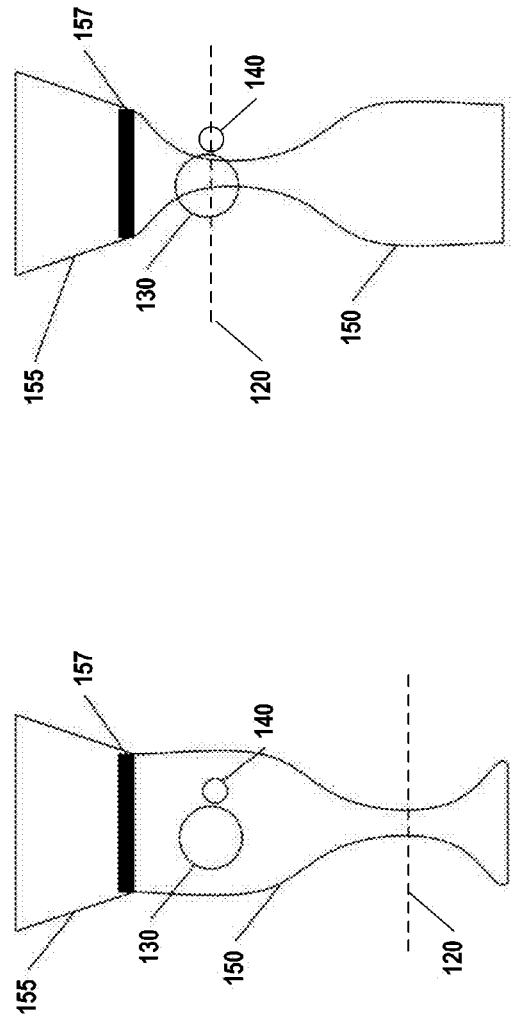
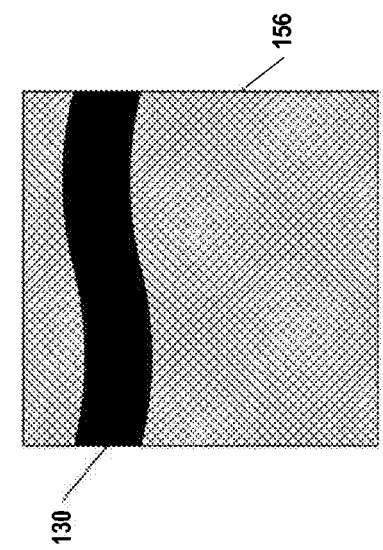
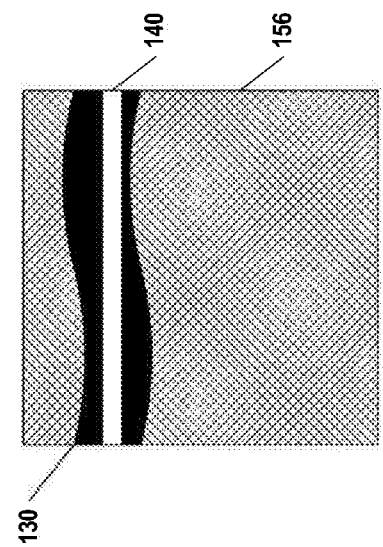

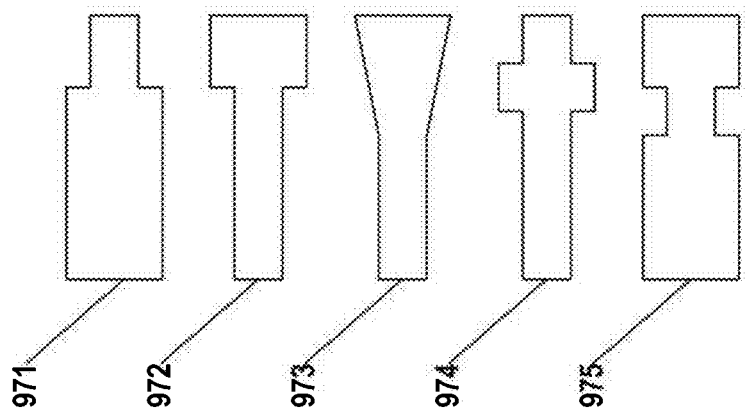

IMAGER FOCUSING BASED ON INTRAOPERATIVE DATA

CROSS-REFERENCE TO RELATED APPLICATION

This application claims the benefit of U.S. Provisional Application No. 61/265,517, entitled "Interactive Control and Display of Ultrasound Imaging Focus," filed Dec. 1, 2009 and U.S. Provisional Application No. 61/265,521, entitled "Medical Imaging and Needle Manipulation," filed Dec. 1, 2009, each of which is incorporated by reference herein in its entirety for all purposes.

BACKGROUND

Various medical imaging modalities are available, such as X-rays, CTs, ultrasound, MRIs, etc. These imaging modalities may be used intraoperatively, during the procedure, or preoperatively, before the procedure starts. X-rays may be used before a procedure starts for preoperative diagnosis—such as diagnosing a fracture of a bone. Ultrasound may be used during a medical procedure to see or find structures inside a patient's body. Consider, for example, the use of ultrasound during prenatal analysis to view the fetus.

Many imagers used in medical procedures may have a focal depth. That is, a depth at which they have better image quality or more focused resolution. A problem with current systems is, however, that areas outside the area of highest focus are produced at lower resolutions. Issues with such imagers may result, such as multiple structures or tissues appearing coincident in the image when they are not actually or truly coincident "in real life", as discussed more below.

SUMMARY

Various embodiments of the systems, methods, computer-readable storage media, and techniques described herein overcome some of these shortcomings of the prior art and provide for imager focusing based on intraoperative data.

Presented herein are methods, systems, devices, computer-readable media, kits, compositions, techniques, and teachings for imager focusing based on intraoperative data. This summary in no way limits the invention herein, but instead is provided to summarize a few of the embodiments. Embodiments include determining pose information for a focusable imager used in a medical scene and pose information for at least one object of interest in the medical scene (simultaneously or in any order). A focal adjustment for the focusable imager is also determined, in some embodiments, based on the pose information for the at least one object of interest and the pose information for the imager. Data to be sent to the focusable imager to adjust the focus of the focal imager may be determined based on the determined focal adjustment for the focusable imager. Numerous other embodiments are described throughout herein, including embodiments where there is also adjusting of the focus of the focusable imager based on the data generated to adjust the focus of the focal imager and/or display of a 3D graphics representation of the object of interest. Embodiments might also include receiving tracking information for the focusable imager or other devices in the scene. In some embodiments, determining the pose information for the at least one object of interest includes accessing stored pose information for an object whose pose was previously indicated (by, e.g., an operator marking a tumor). Many additional embodiments are described below.

Many of the advantages of certain embodiments for imager focusing are described herein. Of course, it is to be understood that not necessarily all such advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

FIGS. 1A and 1B illustrate cross sections of focusable imagers, imaging volumes, and objects of interest.

FIGS. 1C and 1D illustrate images produced by focusable imagers.

FIG. 9 illustrates embodiments of distance indicators.

DETAILED DESCRIPTION OF SPECIFIC EMBODIMENTS

Overview

Figure 2:
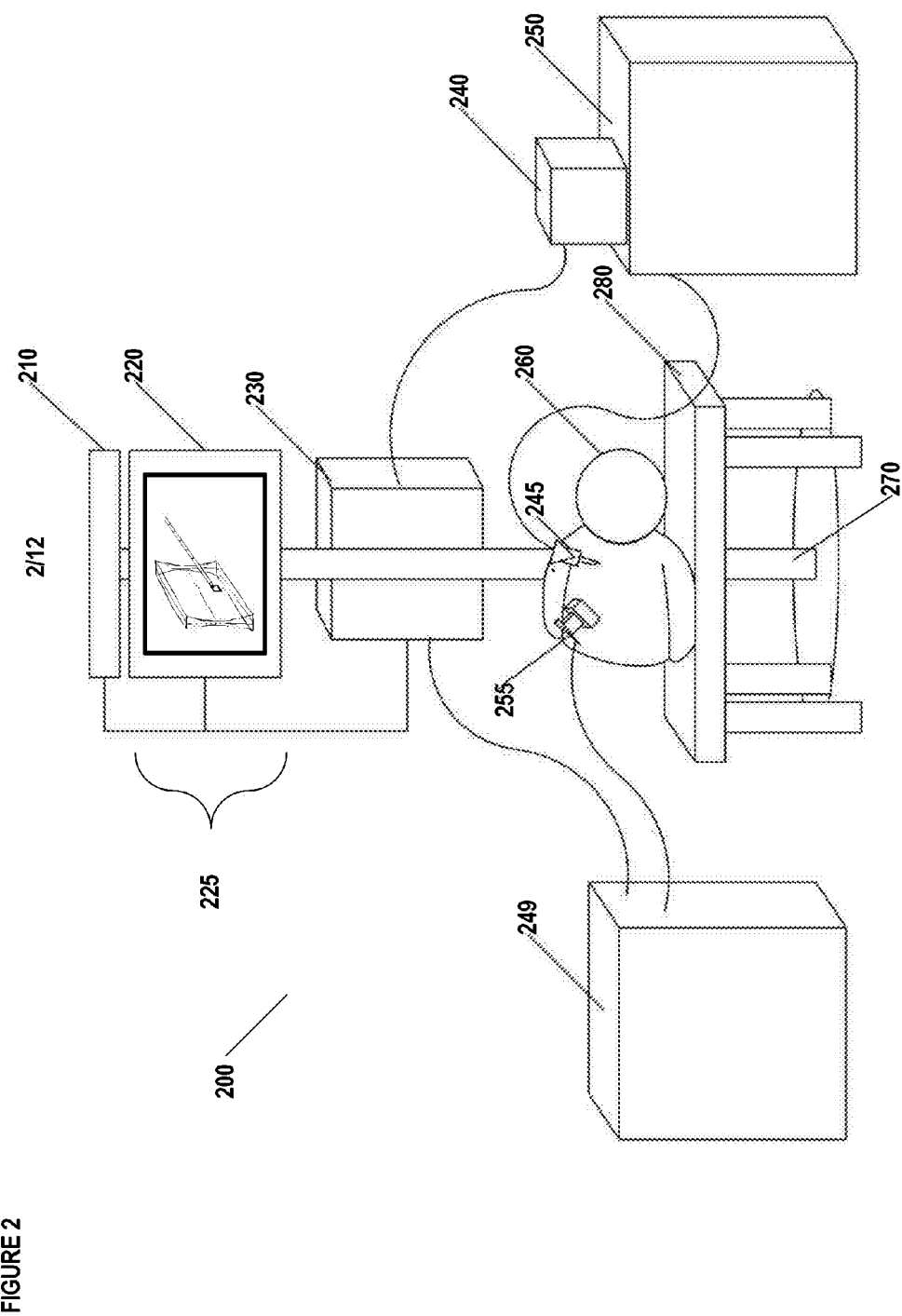
FIG. 2 illustrates an example system for imager focusing based on intraoperative data.

Various methods, systems, devices, computer-readable media, kits, compositions, techniques, teachings and other embodiments for imager focusing based on intraoperative data are disclosed herein.

Imagers typically have imaging planes. The term "imaging plane" as used herein is a broad term and includes its plain and ordinary meaning, and further includes, but is not limited to the plane, area, or volume that is imaged by an imager. Ideally, the imaging plane of an ultrasound transducer would be truly planar. That is not the case, though. Instead, ultrasound transducers, and other imagers, image a volume that is closer to a rectangular volume (as depicted by volumes 1056 in FIGS. 10A-10C). Additionally, ultrasound transducers (and other imagers) have focal depths or areas in the imaged volume that are "thinner" and provide a better resolution. For example, looking to FIG. 1A, we see an abstract depiction of the cross section of an ultrasound transducer 155 and the volume of tissue 150 that is imaged. It is generally the case that the volume of tissue 150 is wider in certain areas and narrower in other areas. For example, the volume 150 of tissue that is imaged may be narrower at a focal depth or focal area 120 and wider in other areas. The ultrasound imager 155 may also include an imaging element 157. The imaging element 157 may include a one-dimensional phased array transducer, two-dimensional phased array transducer or any other imaging element. In some embodiments, discussed more below, the phased array transducer may be focusable. Focusing the imaging element 157 may change the focal depth 120 of the area or volume 150 of tissue to be imaged.

As noted above, FIG. 1A depicts a cross section of an imager 155 and a volume 150 of tissue to be imaged. Also depicted in FIG. 1A is a cross section of a first object 130, such as a blood vessel 130, and a second object 140, such as an ablation needle 140. The blood vessel 130 and the ablation needle 140 are both within the volume of tissue 150 that is captured by the imager 155. The image 156 (in FIG. 1C) produced by the ultrasound system contains a cross section of the blood vessel 130 and the ablation needle 140 seen together as if the ablation needle 140 is inside the blood vessel 130. As is clear in FIG. 1A, however, the ablation needle 140 is not inside the blood vessel 130, but because both the blood vessel 130 and the ablation needle 140 are inside the imaging volume 150, the image 156 produced collocates the two objects, and one cannot decipher whether or not one object is inside the other.

FIG. 1B depicts a cross section of an imager 155 with an imaging element 157 and an imaging volume 150. In FIG. 1B, the focal plane 120 is through the ablation needle 140 and the blood vessel 130. Therefore, the area of highest focus and resolution passes through the blood vessel 130. Therefore, as depicted in FIG. 1D, the blood vessel 130 appears on the image 156 produced by the imager, but the ablation needle 140 from FIG. 1B does not show up in the image 156, letting an operator of the ultrasound transducer 155 (FIG. 1B) determine that the ablation needle 140 is not inside the blood vessel 130.

The various method, systems, techniques, and computer-readable media disclosed herein allow for automatic refocusing of imagers, such as ultrasounds, MRIs and the like, based on objects of interest within the medical scene. The term "medical scene" as used herein is a broad term and includes its plain and ordinary meaning, and further includes, but is not limited to, the site or scene where a medical procedure takes place; a medical site; a medical diagnostic and therapy site; and/or a virtual representation of any of those sites or places. For example, as a surgeon changes the projection of an ablation needle or other device or tool, that projection's intersection with the imaging plane can be used to define the focal plane of the imager. For example, in FIG. 4A there is a patient undergoing a procedure with an ablation needle 445 and ultrasound 455 being used together. These are displayed on display 420 where we see the 3D model of the ablation needle 446 and the image 456 produced by the imager 455. Also visible thereon is an area or object of interest 461. In some embodiments, the area or object of interest 461 may be defined by the intersection of the projection of the ablation needle (or other tool) and the imaging plane or volume of the ultrasound (or other imager). In various embodiments herein, the area or object of interest 461 may be used to define the focal plane of the imager. Therefore, whatever the needle is pointing at will be in highest focus.

Figure 4A:
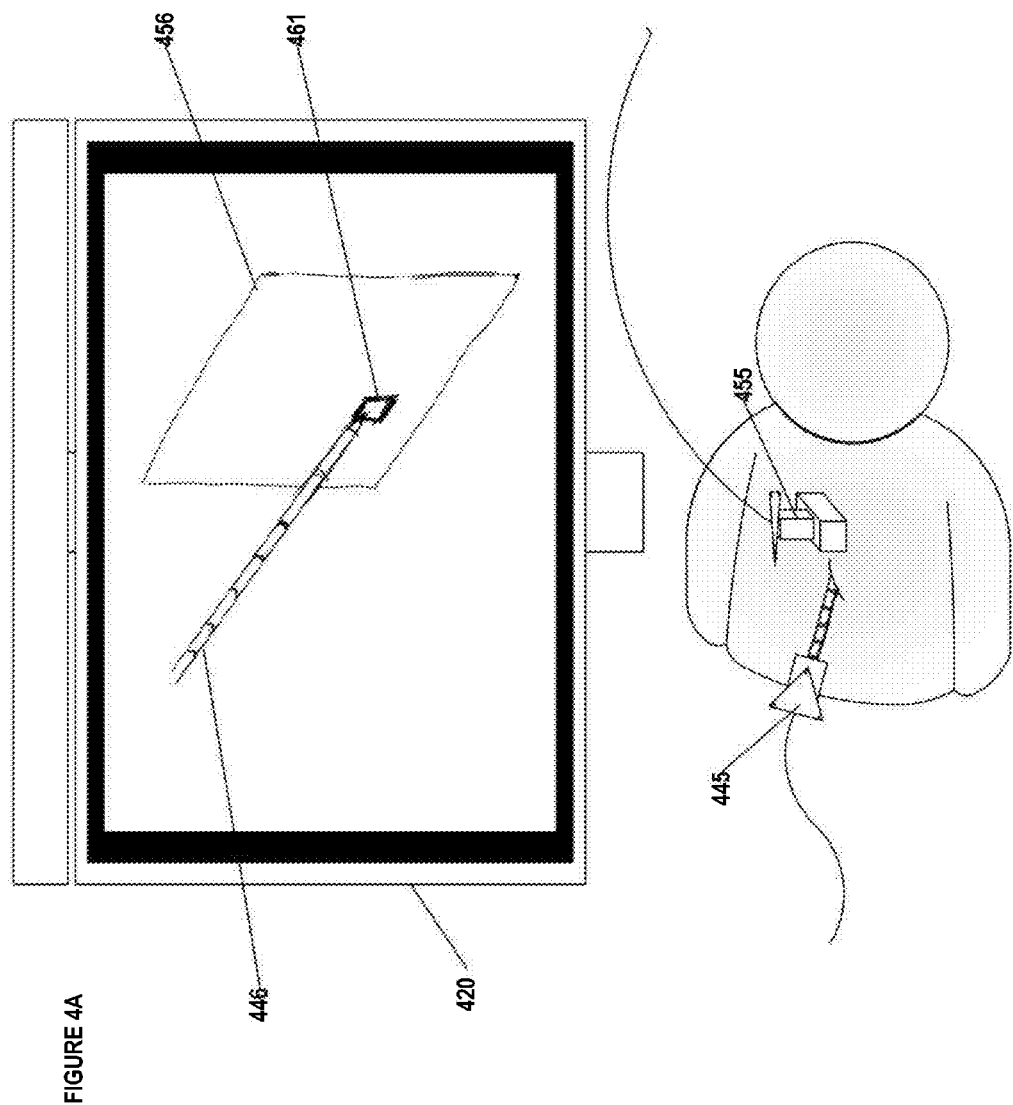
FIG. 4A illustrates a first interface for imager focusing based on intraoperative data.
Figure 4B:
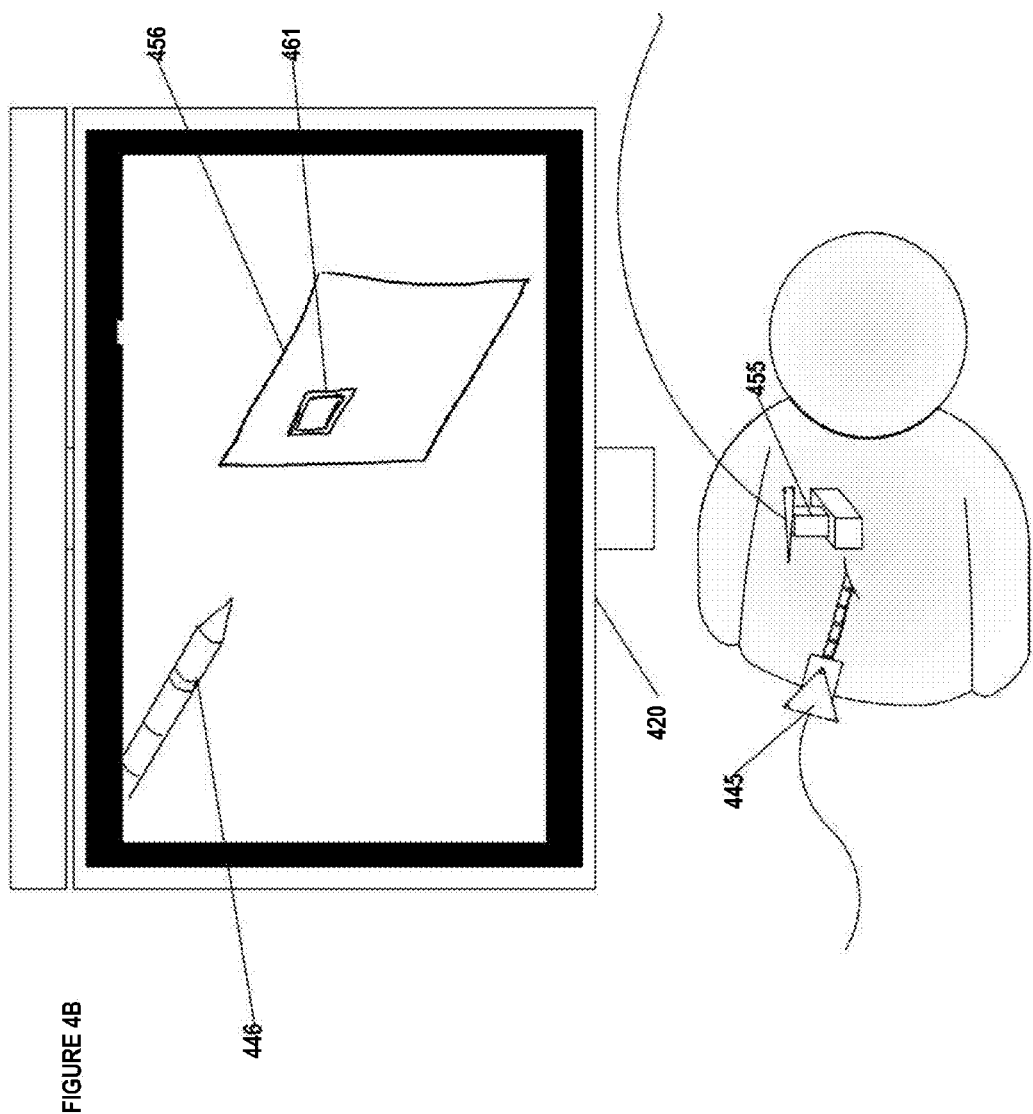
FIG. 4B illustrates a second interface for imager focusing based on intraoperative data.

In various other embodiments, if the needle is not near the plane of the imager, the projection of the needle may provide the guidance, as depicted in FIG. 4B where the 3D model of the needle 446 is distant from the plane of the imager 456, yet there is a target 461 at the intersection of the ray (not pictured) extending from the ablation needle 446 to the image plane 456.

These techniques and teachings herein may be used with any kind of device in any kind of operation. The term "device" as used herein is a broad term and includes its plain and ordinary meaning, and further includes, but is not limited to a medical instrument or an instrument or tool usable in a medical procedure. For example, the device may be an ablation needle, a catheter, cryoablation needle, CUSA dissection tool, a cauterization tool, a knife or scalpel, or any other instrument or tool. Further, the system could use, in some embodiments, a Nintendo Wii or similar controller or use the operator's hand, finger, or eye gaze direction where the hand, finger, or eye gaze are tracked or determined. For example, an operator of the system could point to or look at the image 456 on the display 420 or point to or look at a physical location on the patient to indicate the target 461. Speech recognition could also be used to allow an operator to indicate the location of a target 461. The targets may also be obtained preoperatively and marked, annotated, or highlighted (e.g., such as marking a tumor preoperatively on an MRI or CT scan). Further, there may be multiple objects of interest.

In some embodiments, the imager may be an ultrasound, a cone bean CT, an MRI, optical tomography, confocal microscopy, or any other appropriate imager. The term "focusable imager," as used herein is a broad term that encompasses the plain and ordinary meaning of the term, including without limitation an ultrasound wand that can be focused to have a particular focal depth, or a cone bean CT, MRI, optical tomography, confocal microscopy or other device or tool that can be focused.

The embodiments described herein can be used with preoperative data, including imaging data, data from another procedure, data from another concurrent procedure, and/or with different instrumentation or devices. For example, preoperative data may be displayed along with the imager data on a screen displayed to an operator. In some embodiments, other operative tools or devices may be used and/or may be tracked and displayed to the operator. Various other techniques, embodiments, systems, methods, kits, and computer-readable media are described more below.

System for Imager Focusing Based on Intraoperative Data

FIG. 2 depicts embodiments of a system 200 configured for imager focusing based on intraoperative data. There are numerous other possible embodiments of system 200. For example, numerous of the depicted modules may be joined together to form a single module and may even be implemented in a single computer, machine, or computing device. Further, the position sensing units 210 and 240 may be combined and track all relevant tracked units 245 and movable imaging units 255, as discussed in more detail below. Tracking units may be attached to a medical device 245 (e.g., an ablation needle). Additionally, imaging unit 250 may be excluded and only imaging data from the image guidance unit 230 may be shown on display unit 220. These and other possible embodiments are discussed in more detail below. Numerous other embodiments will be apparent to those skilled in the art and are part of the embodiments herein.

In the pictured embodiment, the system 200 comprises a first position sensing unit 210, a display unit 220, and the second position sensing unit 240 all coupled to an image guidance unit 230. In some embodiments, the first position sensing unit 210, the displaying unit 220, the second position sensing unit 240, and the image guidance unit 230 are all physically connected to stand 270. The image guidance unit 230 may be used to produce images 225 that are displayed on display unit 220. As discussed more below, the images 225 produced on the display unit 220 by the image guidance unit 230 may be made based on imaging data, such as a CT scan, MRI, open-magnet MRI, optical coherence tomography, positron emission tomography ("PET") scans, fluoroscopy, ultrasound, and/or other preoperative or intraoperative anatomical imaging data and 3D anatomical imaging data. The images 225 produced may also be based on intraoperative or realtime data obtained using a movable imaging unit 255, which is coupled to imaging unit 250. The term "realtime" as used herein is a broad term and has its ordinary and customary meaning, including without limitation instantaneously or nearly instantaneously. The use of the term realtime may also mean that actions are performed or data is obtained with the intention to be used immediately, upon the next cycle of a system or control loop, or any other appropriate meaning.

Imaging unit 250 may be coupled to image guidance unit 230. In some embodiments, imaging unit 250 may be coupled to a second display unit 251. The second display unit 251 may display imaging data from imaging unit 250. The imaging data displayed on display unit 220 and displayed on second display unit 251 may be, but are not necessarily, the same. In some embodiments, the imaging unit 250 is an ultrasound machine 250, the movable imaging device 255 is an ultrasound transducer 255 or ultrasound probe 255, and the second display unit 251 is a display associated with the ultrasound machine 250 that displays the ultrasound images from the ultrasound machine 250.

The first position sensing unit 210 may be used to track the position of movable imaging unit 255. Tracking the position of movable imaging unit 255 allows for the determination of the relative pose of imaging data received using the movable imaging unit 255 and imaging unit 250 with that data being sent to image guidance unit 230. For example, image guidance unit 230 may contain CT data which is being updated and deformed based on the relative poses of tracking units as received by the second position sensing unit 240. In such embodiments, the image guidance unit 230 may take in the poses of the tracking units and, from the poses, determine an updated 3D graphics stored in image guidance unit 230. Further, image guidance unit 230 may produce images based on the current ultrasound or other imaging data coming from imaging unit 250 and an updated model determined based on the poses of tracking units. The images produced 225 may be displayed on display unit 220. An example image 225 is shown in FIG. 2.

In some embodiments, a movable imaging unit 255 may not be connected directly to an imagining unit 250, but may instead be connected to image guidance unit 230. The movable imaging unit 255 may be useful for allowing a user to indicate what portions of a first set of imaging data should be displayed. For example, the movable imaging unit 255 may be an ultrasound transducer 255 or a tracked operative needle or other device 255, for example, and may be used by a user to indicate what portions of imaging date, such as a pre-operative CT scan, to show on a display unit 220 as image 225. Further, in some embodiments, there could be a third set of pre-operative imaging data that could be displayed with the first set of imaging data. Additionally, in some embodiments, each of the first and third sets of imaging data could be deformed based on updated positions of the tracking units and the updated, deformed versions of the two sets of imaging data could be shown together or otherwise provide image guidance images 225 for display on display 220.

First position sensing unit 210 may be an optical tracker, a magnetic tracker, or any other appropriate type of position sensing device. For example, in various embodiments, first position sensing unit 210 may be an Ascension Flock of Birds, Nest of Birds, driveBAY, medSAFE, trakSTAR, miniBIRD, MotionSTAR, or pciBIRD. In some embodiments, the first position sensing unit may be an Aurora® Electromagnetic Measurement System using sensor coils. In some embodiments, the first position sensing unit 210 may also be an optical 3D tracking system such as the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, the first position sensing unit 210 may also be an inertial 3D tracking system comprising a compass, accelerometer, tilt sensor and/or gyro, such as the InterSense InertiaCube. The first position sensing unit 210 may sense the position of movable imaging unit 255. If first position sensing unit 210 is an optical tracker, then movable imaging unit 255 may have fiducials placed thereon to make visual position and/or orientation detection possible. If first position sensing unit 210 is a magnetic tracker, then movable imaging unit 255 they have placed thereon magnetic tracking units.

The second position sensing unit 240 and tracking units on tracked device 245 the may together comprise a magnetic tracking system, an optical tracking system, or any other appropriate tracking system. The second position sensing unit 240 and tracking units may be used to track a medical device 245, the deformation of tissue at a target anatomical site on patient 260, or any other appropriate position or device. Patient 260 may be in an operating room, lying on an operating table, such as operating table 280, or in any other appropriate place or position. In various embodiments, second position sensing unit 240 may be an Ascension Flock of Birds, Nest of Birds, driveBAY, medSAFE, trakSTAR, miniBIRD, MotionSTAR, or pciBIRD and tracking units may be magnetic tracking coils. In some embodiments, the second position sensing unit 240 may be an Aurora® Electromagnetic Measurement System using sensor coils for tracking units. In some embodiments, the second position sensing unit 240 may also be an optical 3D tracking system using fiducials as tracking units. Such optical 3D tracking systems may include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, the second position sensing unit 240 may also be an inertial 3D tracking system comprising a compass, accelerometer, tilt sensor and/or gyro, such as the InterSense InertiaCube.

"Tracking unit" as used herein is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below. Tracking units could also include optical position sensing devices such as the HiBall tracking system and the first and second position sensing units 210 and 240 may be part of a HiBall tracking systems. Tracking units may also include a GPS device or signal emitting device that would allow for tracking of the position and, optionally, orientation of the tracking unit. In some embodiments, a signal emitting device might include a radio-frequency identifier (RFID). In such embodiments, the first and/or second position sensing unit 210 and 240 may take in the GPS coordinates of the tracking units or may, for example, triangulate the radio frequency signal being emitted by the RFID associated with tracking units.

In some embodiments, the display unit 220 displays 3D images to a user. This can be accomplished by a stereoscopic display, a lenticular display, or any other appropriate type of display. In some embodiments, an operator may wear head-mounted display in order to receive 3D images from the image guidance unit 230. In such embodiments, display unit 220 may be omitted.

In some undepicted embodiments, there is no first position sensing unit 210 and the poses of both the movable imaging unit 255 and tracked device 245 are determined using the second position sensing unit 240. Similarly, in some embodiments, the first position sensing unit 210 may track the poses of the movable imaging unit 255 and tracked device 245 and the second position sensing unit 240 may not be present. The image guidance may also be performed at least in part using the techniques described in U.S. patent application Ser. No. 11/828,826, filed Jul. 26, 2007, U.S. Pat. No. 7,728,868, U.S. patent application Ser. No. 12/399,899, U.S. patent application Ser. No. 12/483,099, U.S. patent application Ser. No. 12/893,123, U.S. patent application Ser. No. 12/842,261, and/or U.S. patent application Ser. No. 12/703,118, each of which is incorporated by reference herein in its entirety for all purposes.

Processes and Methods for Imager Focusing Based on Intraoperative Data

Figure 3:
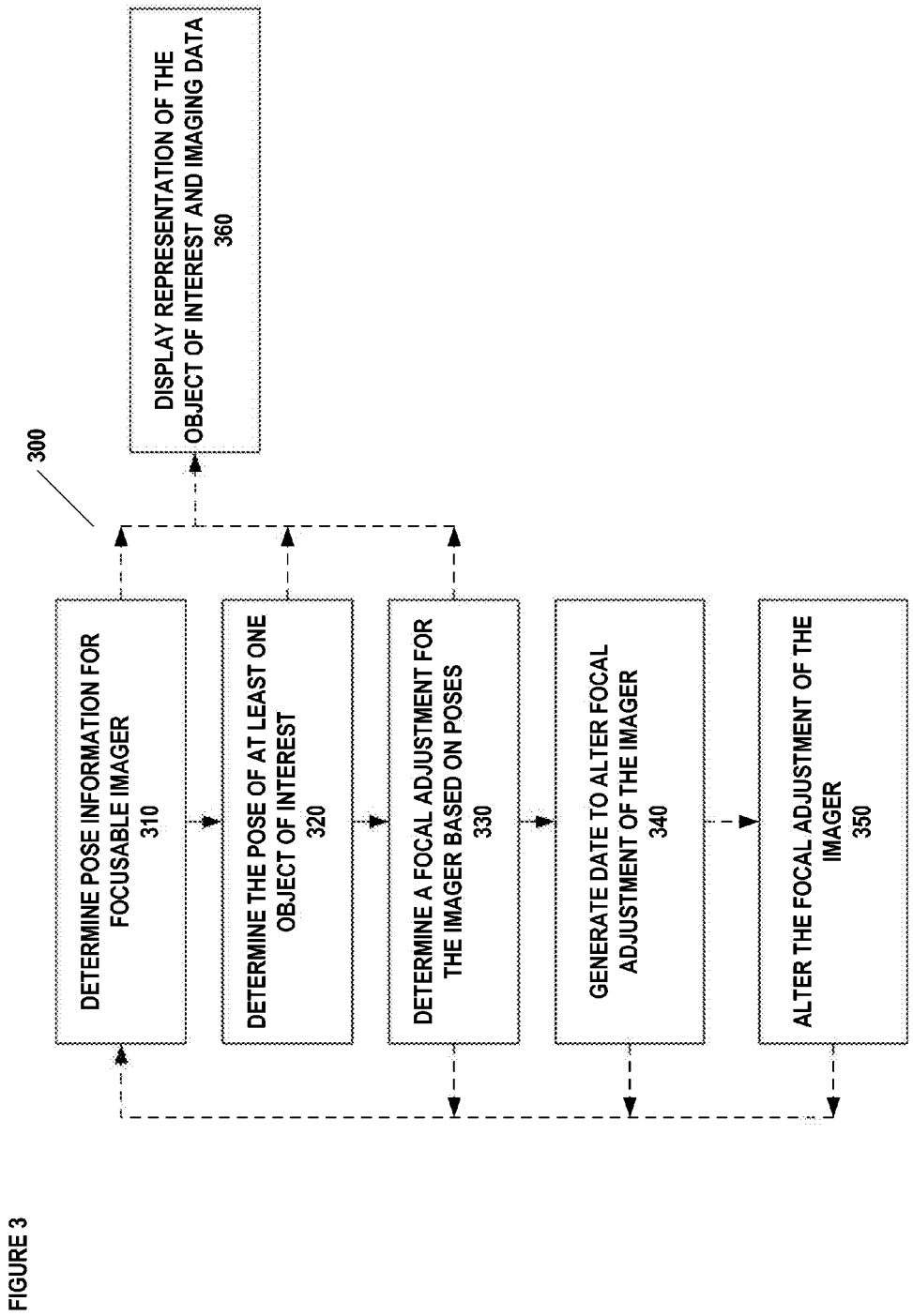
FIG. 3 illustrates a process or method for imager focusing based on intraoperative data.

FIG. 3 depicts embodiments of a process or method 300 for imager focusing based on intraoperative data. In general, the method may include determining the pose of an imager, such as an ultrasound transducer, (block 310) and the pose of a location of interest (block 320). From there, a focal adjustment may be determined (block 330) in order to, for example, better focus the imager on the object of interest. Then data is generated (block 340) and the focus of the imager may be adjusted (block 350). Additionally, imaging data (e.g., a visual representation of position of the in-focus region, the image obtained by the imager, etc.) and/or the object of interest may be displayed (block 360). In operation, various of the blocks presented in process or method 300 in FIG. 3 may be omitted, extra steps may be added, and steps may be performed in different order.

In block 310, pose information for a focusable imager is determined. Determining the pose information for a focusable imager may include receiving tracker information on the pose, position, and/or orientation of a focusable imager, such as imager 255 depicted in FIG. 2. The term "pose information" as used herein includes its plain and ordinary meaning, including position, orientation and/or a combination of the two. "Pose information" can also mean location. As noted above, pose information may be received via optical tracking, magnetic tracking, GPS, triangulation, or any other technique.

In block 320, pose of at least one object of interest is determined. In various embodiments, different objects may be of interest. For example, the object of interest may be an ablation needle, cauterizer, scalpel, catheter, or other device or tool. The pose information may be determined via tracking information (e.g., from the tracked device), as described above. The pose information may be used to determine where an ablation needle, cauterizer or other device or tool is pointing and the intersection of the device or tool's projection and the imager plane. This projected intersection may be the object of interest. For example, turning to FIG. 4A, we see an object of interest 461 as the projection of the ablation needle 446 as it intersects with the imaging plane 456.

Figure 6:
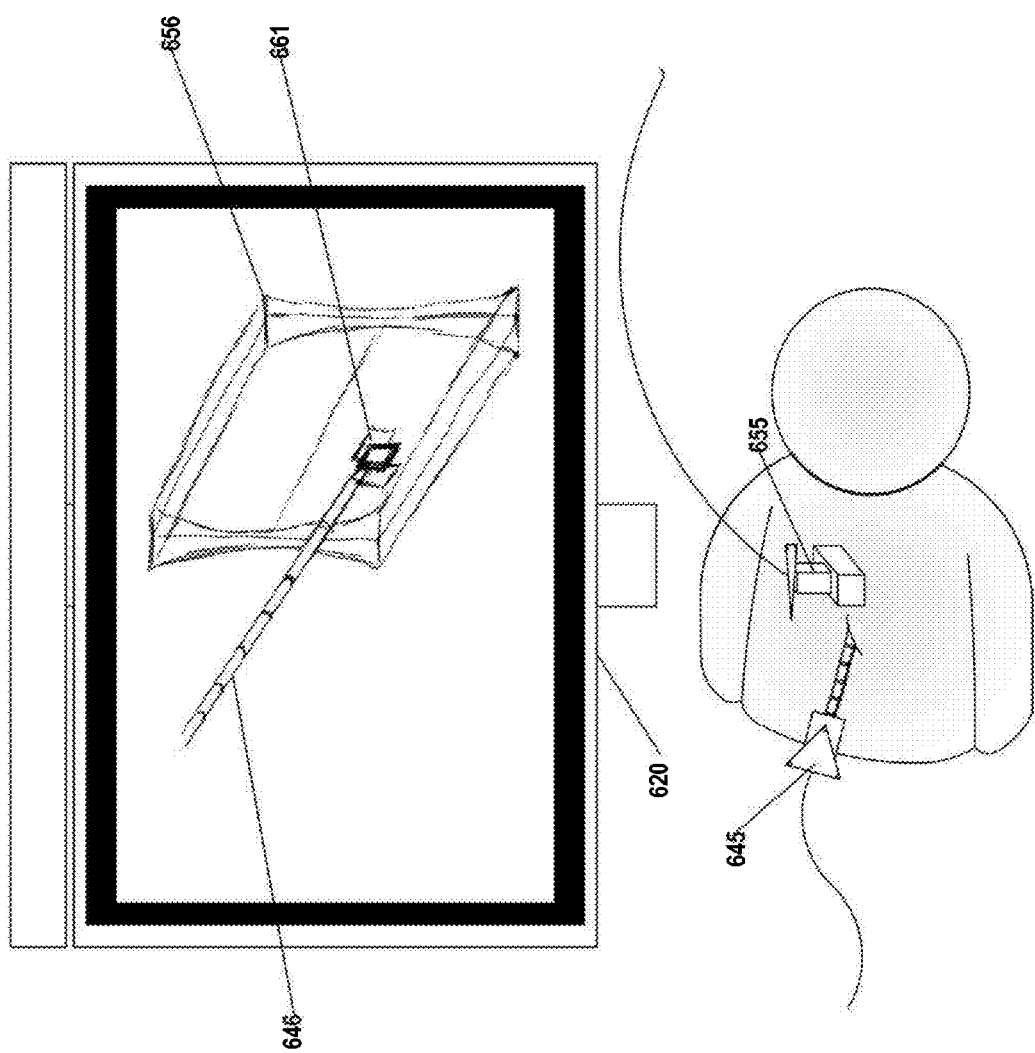
FIG. 6 illustrates a fourth interface for imager focusing based on intraoperative data.
Figure 7:
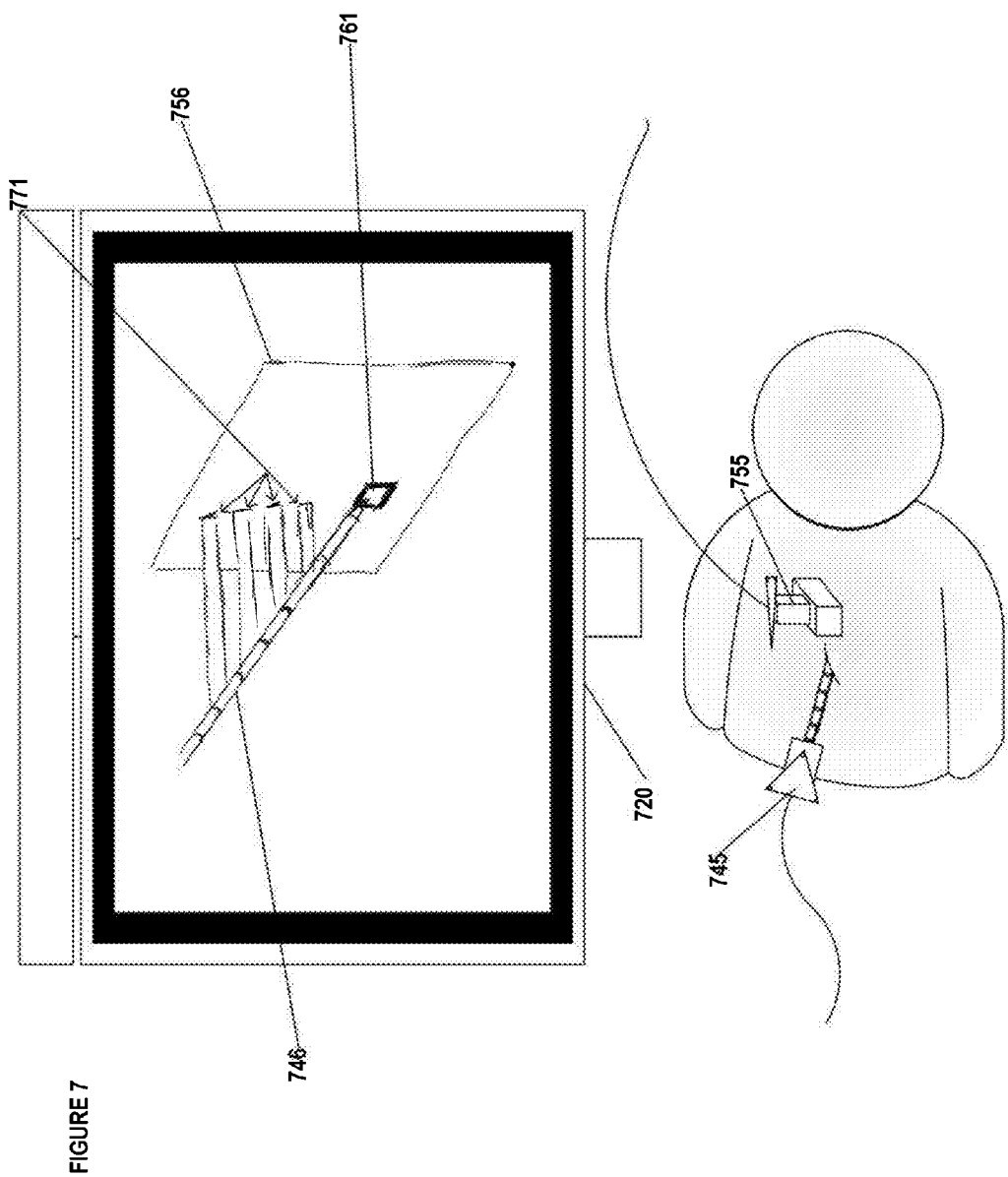
FIG. 7 illustrates a fifth interface for imager focusing based on intraoperative data.

In some embodiments, as an ablation needle (or other device or tool) is moved, the projection of the ablation needle and its intersection with the imager plane may also move. This may cause the focal plane of the imager to move to follow the projection. For example, if an operator, surgeon or other user would like to change the focal depth of an imager, that person may be able to modify the pose of the ablation needle in order to change the pose of the object of interest, which is the intersection of the projection of the ablation needle with the imager plane. As depicted in FIGS. 4A and 4B, in some embodiments, the object of interest, namely the intersection of the projection of the ablation needle and the imager plane, may be displayed as a box, X, circle or any other appropriate marking. In some embodiments, as depicted in FIG. 6, the object of interest 661 may be the projection of the ablation needle 646 onto the imaging volume 656, and it may be displayed as multiple boxes, X's, circles or other indicia 661 on the volume 656. This is depicted as an example, in FIG. 6, as three squares on the closest surface, in the middle, and on the farthest surface of the imaging volume 656.

In some embodiments, the object of interest may be a previously marked, annotated, or highlighted feature within the medical scene. For example, surgeons may mark, circle, or otherwise annotate or indicate tumors, blood vessels, or other features of a patient's anatomy using various techniques. This data for the annotation, highlights, and markings may be used within the medical scene to indicate various areas of interest. Consider, for example, a liver with a single tumor. That tumor may be highlighted, marked, or annotated in a way that the pose of that tumor is known. As the operator moves the imager (such as the ultrasound transducer) around the outside of the patient's body, the focal plane for the imager may be modified to match or closely match the position of the marked tumor. In this way, the highest resolution and best focus of the imager will always be at or near the object of interest, in this case the tumor. There may also be multiple objects of interest, such as multiple tumors, that are each marked, highlighted, etc. In some embodiments, there may be objects of interest that are marked, annotated, or highlighted in addition to and/or instead of the area of interest indicated by the operator using an ablation needle, cauterizing tool, catheter, finger, eye gaze, etc. That is, for example, there may be three tumors and a vein marked, and the operator may be able to point using a cauterizer to indicate another area of interest. Some or all of these poses may be determined in block 320.

In block 330, a focal adjustment for the imager is determined based on the pose or the poses of the at least one object of interest. For example, if there is a single object of interest and the desire is to have the focus on that object of interest, then based on the pose of the object of interest the focal plane may be defined. The focal plane may, for example, be defined to pass through the center of the object of interest or to pass near the object of interest. Turning back to FIG. 1B, for example, if the object of interest 140 is the ablation needle or its projection, then the focal plane 120 may be moved to pass through the center of that object of interest 140. Turning to FIGS. 4A and 4B, if the object of interest is the intersection of the projected ray (not depicted) from the ablation needle 446 and the imaging plane 456, said object of interest being projection 461, then the focal plane may be determined to pass through or near the object of interest 461. Turning to FIG. 2, if an operator is manipulating the imager 255 and an ablation needle 245, and the object of interest is the intersection of the projection of the ablation needle with the imager, then as the operator manipulates one or both of the imager 255 and the ablation needle 245, the object of interest will move and the focus of the imager 255 will be changed.

In some embodiments, determining a focal adjustment for the imager based on one or more poses comprises determining a series of focal adjustments to be used sequentially over time. For example, if there are multiple objects of interest, then the imager may be focused on each of them in series and, thereby receiving at least some images that are focused on each object. For example, if there are three tumors in a volume that is being imaged by the imager, then the imager may first focus on the first tumor, then focus on the second, and finally focus on the third. In that way the imager will obtain a high resolution image for each of the three objects of interest (tumors) in turn.

In some embodiments, a series of focal adjustments may be determined to get focus in areas around the object of interest. For example, if there is a single object of interest, a first image may be focused just above the object of interest, a second through the object of interest, and a third below the object of interest. Some embodiments will continually scan the volume of interest by changing the focus in fixed intervals and/or for fixed distances. For example, if the image volume is four inches tall, it may first focus one inch down, then focus two inches down, and then focus three inches down, and cycle through that pattern to provide a varying focus over time. In some embodiments, this cycling may be modified so that more of the steps of the cycling are focused at or near the object of interest and fewer of these steps of the cycle are focused away from the object of interest.

In some embodiments, the angle of projection of the ultrasound waves within the plane of the imager may be modified. For example, FIG. 10A illustrates the depiction of the ultrasound waves 1081 leaving the imager 1050 via the imaging element 1057 to produce an imaging volume or plane 1056 in order to capture an image at least in part of an ablation needle 1046. Typically, the sound waves of an ultrasound will travel perpendicular to the imaging element 1057. The imaging element 1057 may be, for example, a one-dimensional phased array transducer. In some embodiments, the one-dimensional phased array transducer can be manipulated so that the waves traveling from the transducer can be focused onto an object of interest.

Figure 10C:
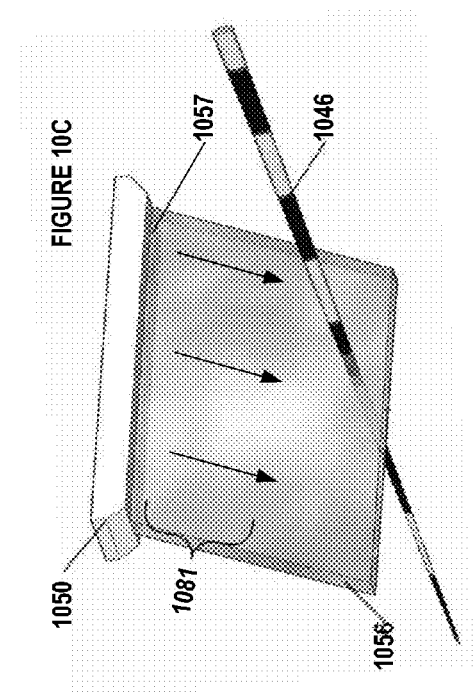
FIGS. 10A-10C illustrate focusable imagers with directable imaging elements.
Figure 10A:
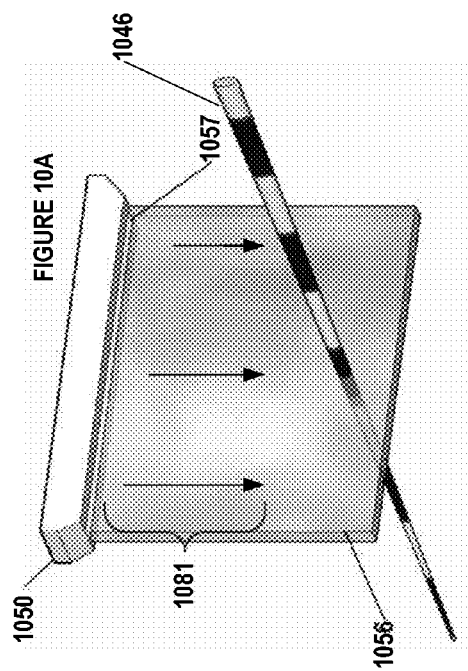
Figure 10B:
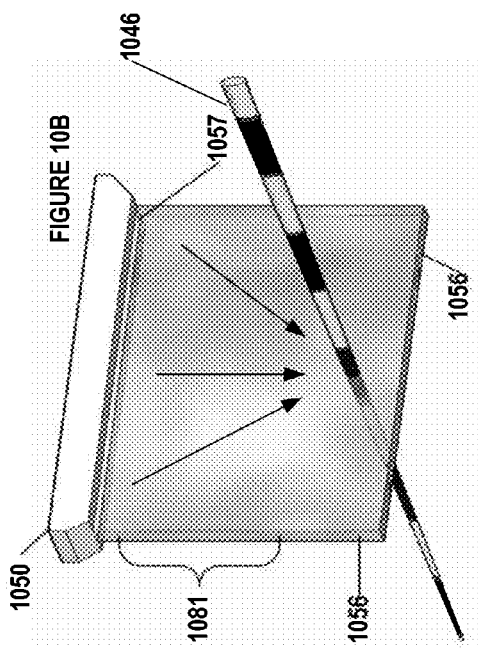

FIG. 10C illustrates that the imaging element 1057 can be reconfigured to direct the imaging waves (e.g., pressure or energy), in a different direction, as indicated by arrows 1081, in order to change the angle at which the rays from the element 1057 are hitting the object of interest, in this case, an ablation needle 1046. One reason to modify the angle at which the waves from an imaging element are hitting an object of interest is so that the angle of propagation at or more closely approximating a perpendicular angle (e.g., around 90°) to the surface of the object. In some embodiments and with some imagers, the closer imaging is to a perpendicular angle, the more vividly or better quality the resulting images will be, and the more likely the user will detect the object in the resulting image The embodiments discussed with respect to FIGS. 10A-10C help overcome some issues associated with objects at oblique angles by refocusing or changing the angle at which an object of interest is being imaged, thereby improving the quality of the image that can be obtained. For example, looking to FIG. 10B, the rays 1081 from imager 1050 are focused towards the intersection of the ablation needle 1046 with the ultrasound volume 1056. In this way, more of the resolution of the ultrasound will be focused on the object of interest 1046.

In some embodiments, similar techniques can be used for biplane or 2D arrays of transducers. For example, all of the transducers in a 2D array of transducers could be focused towards an object of interest or one or two dimensions in the 2D array of transducers could be modified, in an angular sense, in order to better image an object of interest. For a biplane imager, one or both of the planes could each be separately modified as discussed above with respect to FIGS. 10A-10C.

After the focal adjustments have been determined in block 330, then in block 340, data is generated to alter the focal adjustments of the imager. For example, in some embodiments the imager may have an API or application program interface, an electronic interface, etc. Data can be generated to conform to that interface in order to alter the focal adjustment of the imager.

In some embodiments, the data generated in block 340 may be sent to the imager or the imager's interface, and the imager or the imager's interface may interact with the imager and/or the imaging elements in order to alter the focal adjustments, as depicted in block 350 of FIG. 3. After generating the data to alter the focal adjustments of the imager in block 340, or altering the focal adjustments of the imager in block 350, method 300 may start again from block 310, 320 (not pictured), or any of the other blocks (not pictured). For example, after generating the data to alter the focal adjustments (block 340) or determining a focal adjustment for the imager based on the poses (block 330), the method 300 may again return to determine new pose information for the focusable imager and determine the pose of at least one object of interest, if there is any new pose information.

Additionally, after determining the poses of the imager and/or the objects of interest at any iteration of method 300, a representation of the imager and the object of interest may be displayed in block 360 (depicted as occurring after block 310 or 320 in FIG. 3).

Figure 5:
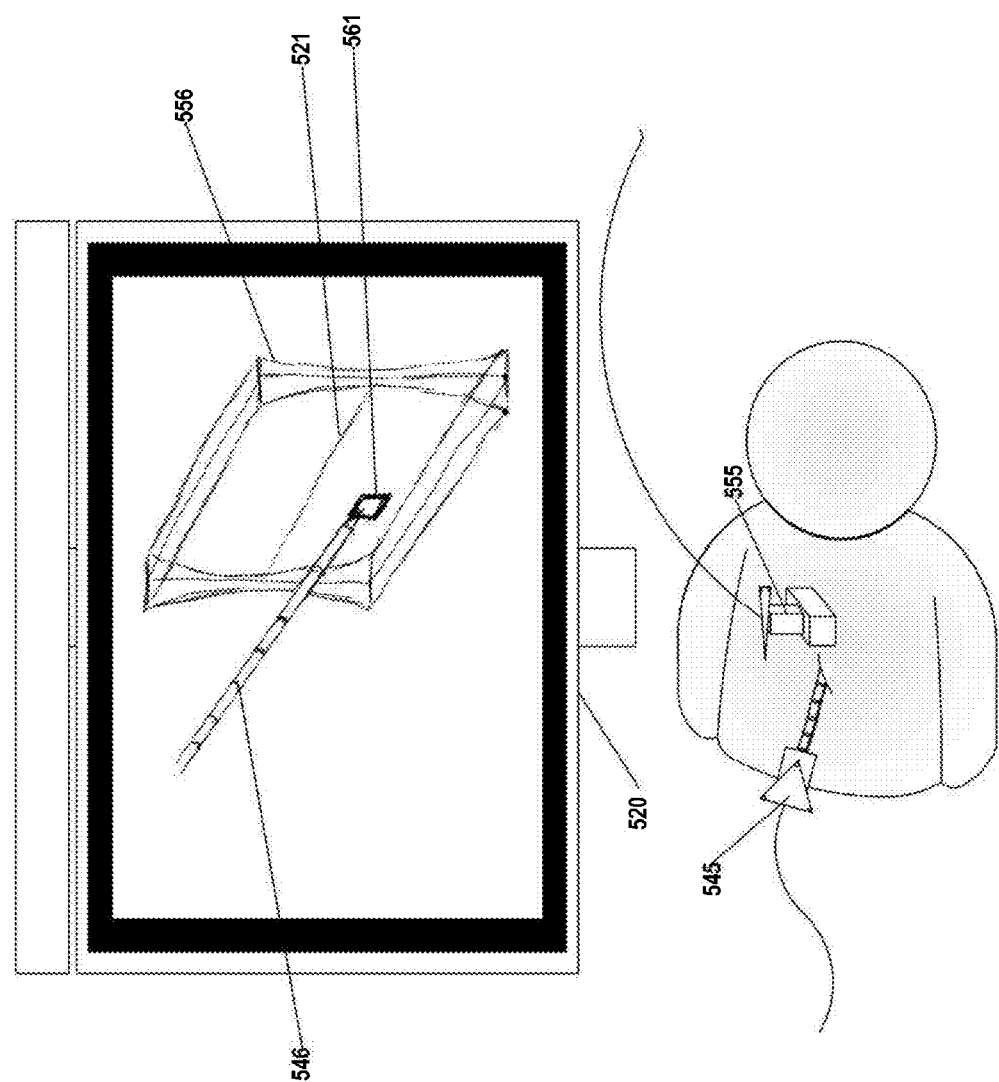
FIG. 5 illustrates a third interface for imager focusing based on intraoperative data.

Various embodiments of the types of displays that can be used in block 360 are depicted in the figures herein. For example, as discussed above, in FIGS. 4A and 4B there is an ablation needle 446 being depicted on a display 420 as well as the image from the imager 456 and the object of interest 461. In FIG. 5, display 520 displays an object of interest 561 along with the ablation needled 546 and the imaging volume 556. Here the imaging volume 556 is being displayed with an indication 521 of the focal depth of the imager. FIG. 5 may be an example of the imager iterating over a series of focal depths 521 and, in this particular instance, the focal depth 521 is above the object of interest 561. FIG. 6 depicts a display 620 showing device or tool 646. Object of interest 661 is displayed in the center of the imaging volume 656 as well as on the surfaces of the imaging volume 656—as three squares on the display 620.

Distance Indicators

In some embodiments, it can be helpful to an operator to have bars or other indicators showing the depth or distance between a device 746 and the image plane 756. These are depicted as bars 771 on display 720. In some embodiments, the bars between the device 746 and the image plane 756 are shorter when the device is closer to the image 756, and the bars 771 are longer when the device 746 is further away from the imager 756.

Figure 8:
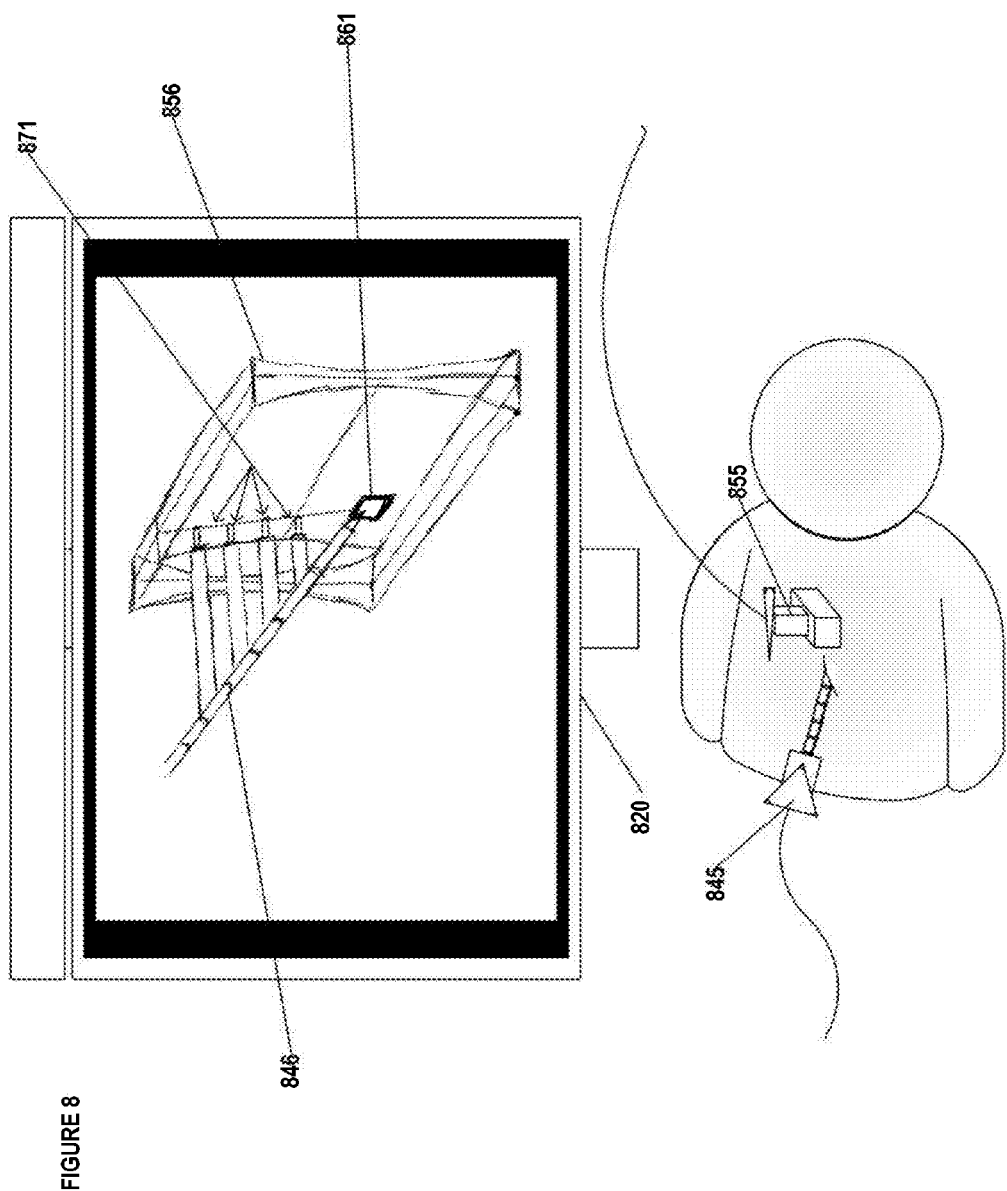
FIG. 8 illustrates a sixth interface for imager focusing based on intraoperative data.

In some embodiments, as depicted in FIG. 8, the indicators 871 may be more complex than simple bars. In FIG. 8, indicators 871 are thicker outside of the image volume 856 (e.g., between the image volume 856 and the cauterizer 846). Inside the image volume 856, the indicators 871 are narrower. This differentiation of the size of the indicators 871 may be useful to show the operator both the distance of the cauterizer 846 from the imaging volume 856 as well as the thickness of the imaging volume 856 at various points in the imaging volume. FIG. 9 shows multiple different indicators 971-975, each of which may be used as described above. Various other embodiments, techniques, methods and systems will be clear from the disclosure herein and are considered part of the embodiments disclosed herein.

Projecting Placement

In some cases, particularly with the rapidly growing number of obese patients the needle or other surgical device may not be long enough to reach the target or object of interest when approaching from an "easy" or convenient angle, and so the physician or other operator must find creative ways of approaching the target. In some embodiments herein, the system may make it clear to an operator whether the device, when inserted, will reach a desired feature in the ultrasound image. In certain procedures and embodiments, there may be prediction information related to the surgical instruments. In the context of scalpel movement, this may be the location that the scalpel will hit if a physician continues to move the scalpel in a particular direction. In the context of ablation, this may be the projected needle placement if it is driven along its central axis. FIG. 11A illustrates the projected drive trajectory 1147 of a needle 1146. If a physician is driving an ablation needle into tissue (said tissue not pictured in FIG. 11A), then she may want to know where the needle will be driven. In some embodiments, the projected drive 1147 of a needle 1146 may be depicted on the display 1120 and may show the physician the projected path 1147 that the needle will take if it is driven along its central axis—and the depth it may travel.

Figure 11B:
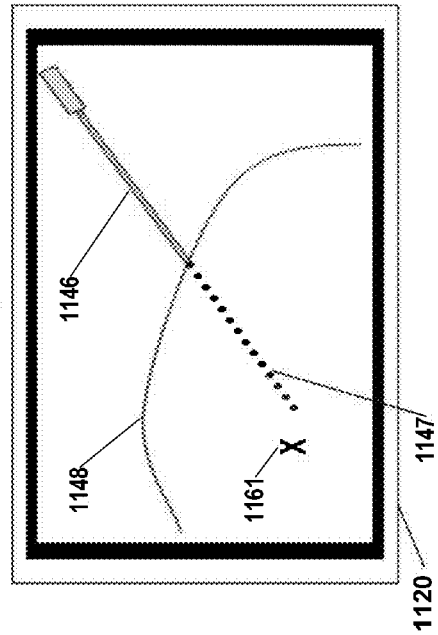
FIGS. 11A-11C illustrate three interfaces for imager focusing based on intraoperative data.
Figure 11A:
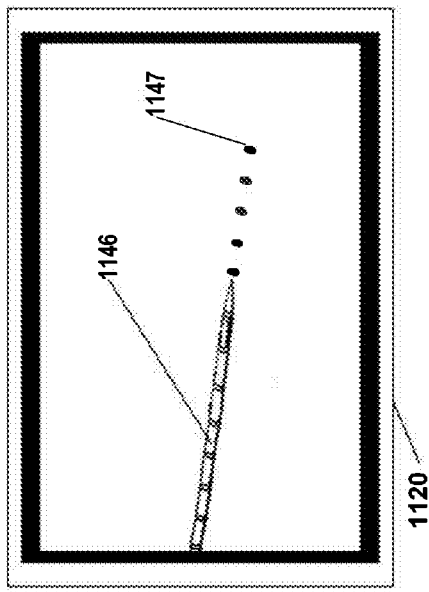

In some embodiments, the system may draw the trajectory of the needle extending beyond the tip, extending approximately one needle-length beyond the tip (See, e.g., FIG. 11B). Then when the physician aims the needle 1146 (scalpel, cauterizer, or any other device or tool) toward the target 1161, resting the tip on the patients' skin or organ surface 1148 before driving the needle 1146, the trajectory indicator 1147 will indicate whether the needle 1146 will reach the target 1161 if driven fully in the same direction. In some embodiments, in order to aid the physician in placing or orienting a needle, an image guidance system, such as that depicted in FIG. 2, may draw a number of rings about the axis of the needle shaft, extrapolated beyond its tip, as depicted in FIG. 11A.

Figure 11C:
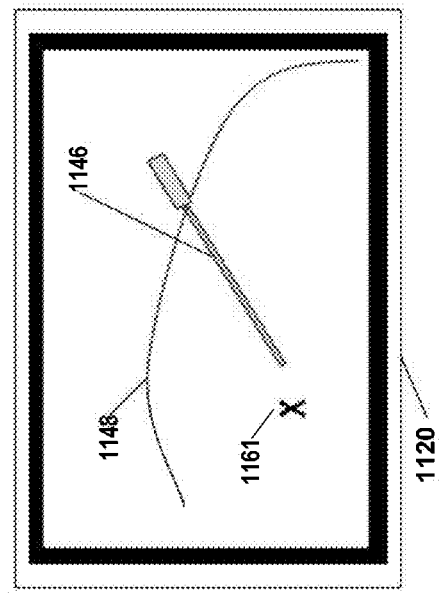

A physician may view and manipulate the position and orientation of the needle 1146 and its expected drive projection (via its displayed projected trajectory 1147) before it enters the patient's tissue. In some embodiments, this is accomplished by the doctor positioning the virtual rings in the drive projection such that they are co-incident (or pass through) the ultrasound representation of a target, such as a tumor that the doctor has spotted in the ultrasound. This may allow the physician to verify that the needle is properly aimed at the target and can drive the needle forward into the tissue such that it reaches its desired target or destination. For example, if the doctor spotted a tumor 1161 in the ultrasound image on display 1120 in FIG. 11B, she may be able to reposition or align the ablation needle 1146 such that the drive projection rings on display 1120 intersected or otherwise indicate that the needle, if driven straight, will reach the tumor. In the example of FIG. 11B, because the projection 1147 does not reach the tumor 1161 it appears that the needle 1146 would not reach the tumor 1161 when driven, as depicted in FIG. 11C.

The rings of a projection 1147 may be spaced at regular (e.g., 0.5, 1, or 2 cm) intervals to provide the physician with visual cues regarding the distance from the needle tip to the targeted anatomy. In some embodiments, the spacing of the rings may indicate other aspects of the data, such as the drive speed of the needle, the density of the tissue, the distance to a landmark, such as a target 1161, or any other appropriate guidance data or property. In some embodiments, the rings or other trajectory indicator may extend beyond the needle tip, by a distance equal to the length of the needle-shaft. This way, the user knows if the needle is long enough to reach the target—even before the tip enters the patient. That is, in some embodiments, if the rings do not reach the target with the tip still outside the body, then the tip won't reach the target when the entire length shaft is inserted into the body.

Other display markers may be used to show trajectory, such as a dashed, dotted, or solid line, transparent needle shaft, point cloud, wire frame, etc. In some embodiments, three-dimensional rings may be used and provide depth cues and obscure little of the ultrasound image. Virtual rings or other virtual markers may be displayed semi-transparently, so that they obscure less of the ultrasound image than an opaque marker would.

Other prediction information may also be displayed. For example, if a scalpel is being tracked by the image guidance system, then a cutting plane corresponding to the scalpel may be displayed (not pictured). Such a cutting plan may be coplanar with the blade of the scalpel and may project from the blade of the scalpel. For example, the projected cutting plane may show where the scalpel would cut if it were the doctor were to advance the scalpel. Similar prediction information may be estimable or determinable for cauterizers, lasers, and numerous other surgical instruments.

Other Embodiments

The processes and systems described herein may be performed on or encompass various types of hardware, such as computing devices. In some embodiments, position sensing units 210 and 240, display unit 220, image guidance unit 230, second display unit 251, and/or any other module or unit of embodiments herein may each be separate computing devices, applications, or processes or may run as part of the same computing devices, applications, or processes—or one of more may be combined to run as part of one application or process—and/or each or one or more may be part of or run on a computing device. Computing devices may include a bus or other communication mechanism for communicating information, and a processor coupled with the bus for processing information. The computing devices may have a main memory, such as a random access memory or other dynamic storage device, coupled to the bus. The main memory may be used to store instructions and temporary variables. The computing devices may also include a read-only memory or other static storage device coupled to the bus for storing static information and instructions. The computer systems may also be coupled to a display, such as a CRT, LCD monitor, projector, or stereoscopic display. Input devices may also be coupled to the computing devices. These input devices may include a mouse, a trackball, foot pedals, touch screen or tablet, drawing tablet, or cursor direction keys.

Each computing device may be implemented using one or more physical computers, processors, embedded devices, field programmable gate arrays (FPGAs) or computer systems or a combination or portions thereof. The instructions executed by the computing device may also be read in from a computer-readable medium. The computer-readable medium may be non-transitory, such as a CD, DVD, optical or magnetic disk, flash memory, laserdisc, carrier wave, or any other medium that is readable by the computing device. In some embodiments, hardwired circuitry may be used in place of or in combination with software instructions executed by the processor. Communication among modules, systems, devices, and elements may be over a direct or switched connections, and wired or wireless networks or connections, via directly connected wires, or any other appropriate communication mechanism. Transmission of information may be performed on the hardware layer using any appropriate system, device, or protocol, including those related to or utilizing Firewire, PCI, PCI express, CardBus, USB, CAN, SCSI, IDA, RS232, RS422, RS485, 802.11, etc. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, DICOM, DICOS, secure sockets, VPN, encrypted or unencrypted pipes, MIME, SMTP, MIME Multipart/Related Content-type, SQL, etc.

Any appropriate 3D graphics processing may be used for displaying or rendering, including processing based on OpenGL, Direct3D, Java 3D, etc. Whole, partial, or modified 3D graphics packages may also be used, such packages including 3DS Max, SolidWorks, Maya, Form Z, Cybermotion 3D, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements, and/or states are included or are to be performed in any particular embodiment.

Any process descriptions, elements, or blocks in the processes, methods, and flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method for imager focusing based on intraoperative data, implemented on one or more computing devices, comprising:
   determining, using the one or more computing devices, position and orientation of an imaging plane of a focusable imager used in a medical scene based at least in part on a detected position and orientation of a first tracking device coupled to the focusable imager;
   determining, using the one or more computing devices, position and orientation of a medical device used in the medical scene based at least in part on a detected position and orientation of a second tracking device coupled to the medical device;
   determining, using the one or more computing devices, an intersection of the imaging plane and a central axis of the medical device based at least in part on the determined position and orientation of the imaging plane and the determined position and orientation of the medical device;
   determining, using the one or more computing devices, position and orientation of at least one object of interest in the medical scene based at least in part on the determined intersection of the imaging plane and the central axis of the medical device;
   determining, using the one or more computing devices, a focal adjustment for the focusable imager based at least in part on the determined position and orientation of the at least one object of interest and a focal plane of the focusable imager; and
   causing the focusable imager to adjust the focal plane based at least in part on the determined focal adjustment for the focusable imager.

2. The method of claim 1, further comprising displaying a 3D graphics representation of the object of interest.

3. The method of claim 1, wherein determining the position and orientation of the at least one object of interest comprises accessing stored position and orientation of an object whose position and orientation was previously indicated.

4. The method of claim 3, wherein accessing stored position and orientation of an already-known object of interest comprises accessing stored position and orientation of at least one of a highlight, marking, or annotation of the already-known object of interest.

5. The method of claim 1, wherein the medical device comprises a tracked ablation needle.

6. The method of claim 1, wherein determining the pose for the at least one object of interest comprises determining position and orientation of a body part of an operator.

7. The method of claim 1, wherein determining the focal adjustment based at least in part on the position and orientation of the at least one object of interest comprises determining a trajectory of the medical device onto an imaging plane associated with the imager.

8. The method of claim 1, wherein determining the focal adjustment based at least in part on the position and orientation of the at least one object of interest comprises determining a series of focal adjustments to be used over time based at least in part on the position and orientation of the at least one object of interest.

9. The method of claim 1, wherein determining the focal adjustment based at least in part on the position and orientation of the at least one object of interest comprises determining a depth of focus for the focusable imager based at least in part on the position and orientation of the at least one object of interest.

10. The method of claim 1, wherein determining the focal adjustment based at least in part on the position and orientation of the at least one object of interest comprises determining an angle for directing an imaging element of the focusable imager.

11. The method of claim 1, wherein the at least one object of interest comprises two or more objects of interest.

12. The method of claim 11, wherein determining the focal adjustment based at least in part on the position and orientation of the at least one object of interest comprises determining two or more focal adjustments based at least in part on the two or more objects of interest.

13. A non-transitory computer-readable medium comprising computer-executable instructions that when executed by one or more computing devices, cause the one or more computing devices to:
   determine position and orientation of an imaging plane of a focusable imager used in a medical scene based at least in part on a detected position and orientation of a first tracking device coupled to the focusable imager;
   determine position and orientation of a medical device used in the medical scene based at least in part on a detected position and orientation of a second tracking device coupled to the medical device;
   determine an intersection of the imaging plane and a central axis of the medical device based at least in part on the determined position and orientation of the imaging plane and the determined position and orientation of the medical device;
   determine position and orientation of at least one object of interest in the medical scene based at least in part on the determined intersection of the imaging plane and the central axis of the medical device;
   determine a focal adjustment for the focusable imager based at least in part on the position and orientation of the at least one object of interest and the position and orientation of a focal plane of the focusable imager; and
   cause the focusable imager to adjust the focal plane the focusable imager based at least in part on the determined focal adjustment for the focusable imager.

14. The non-transitory computer-readable medium of claim 13, the computer-executable instructions further cause the one or more computing devices to display a 3D graphics representation of the object of interest.

15. The non-transitory computer-readable medium of claim 13, wherein to determine the position and orientation of the at least one object of interest the computer-executable instructions cause the one or more computing devices to access stored position and orientation of an object whose pose was previously indicated.

16. A system comprising one or more computing devices, said one or more computing devices being configured to:
   determine position and orientation of an imaging plane of a focusable imager used in a medical scene based at least in part on a detected position and orientation of a first tracking device coupled to the focusable imager;
   determine position and orientation of a medical device used in the medical scene based at least in part on a detected position and orientation of a second tracking device coupled to the medical device;
   determine an intersection of the imaging plane and a central axis of the medical device based at least in part on the determined position and orientation of the imaging plane and the determined position and orientation of the medical device;
   determine position and orientation of at least one object of interest in the medical scene based at least in part on the determined intersection of the imaging plane and the central axis of the medical device;
   determine a focal adjustment for the focusable imager based at least in part on the position and orientation of the at least one object of interest and the position and orientation of a focal plane of the focusable imager; and
   cause the focusable imager to adjust the focal plane of the focusable imager based at least in part on the determined focal adjustment for the focusable imager.

17. The system of claim 16, wherein the at least one medical device comprises a tracked ablation needle.

18. The system of claim 16, wherein to determine the focal adjustment based at least in part on the position and orientation of the at least one object of interest, the one or more computing devices are configured to determine a series of focal adjustments to be used over time based at least in part on the position and orientation of the at least one object of interest.

* * * * *